(12) United States Patent  (10) Patent No.: US 7,695,277 B1
Stevens  (45) Date of Patent: Apr. 13, 2010

(54) ORTHODONTIC BRACKET WITH FRANGIBLE COVER MECHANISM

(75) Inventor: Michael Stevens, Littleton, CO (US)

(73) Assignee: RMO, Inc., Denver, CO (US)

( * ) Notice: Subject to any disclaimer, the term of this patent is extended or adjusted under 35 U.S.C. 154(b) by 638 days.

(21) Appl. No.: 11/260,923

(22) Filed: Oct. 27, 2005

Related U.S. Application Data

(60) Provisional application No. 60/623,715, filed on Oct. 28, 2004.

(51) Int. Cl.
A61C 3/00 (2006.01)
(52) U.S. Cl. ............................................. 433/11
(58) Field of Classification Search ............ 433/8, 433/10–11, 14
See application file for complete search history.

(56) References Cited

U.S. PATENT DOCUMENTS

| | | |
|---|---|---|
| 1,890,487 A | 12/1932 | Angle |
| 3,028,671 A | 4/1962 | Berger |
| 3,391,461 A | 7/1968 | Johnson |
| 3,435,527 A | 4/1969 | Kesling |
| 3,494,034 A | 2/1970 | Kesling |
| 3,504,438 A | 4/1970 | Wittman et al. |
| 3,526,961 A | 9/1970 | Kesling |
| 3,765,091 A | 10/1973 | Northcutt |
| 3,838,514 A | 10/1974 | Polak |
| 3,854,207 A | 12/1974 | Wildman |
| 3,874,080 A | 4/1975 | Wallshein |
| 3,964,156 A | 6/1976 | Williams et al. |
| 4,028,809 A | 6/1977 | Wallshein |
| 4,103,423 A | 8/1978 | Kessel |
| 4,134,208 A | 1/1979 | Pearlman |
| 4,172,999 A | 10/1979 | Leidich |
| 4,193,195 A | 3/1980 | Merkel et al. |
| 4,197,642 A | 4/1980 | Wallshein |
| 4,219,617 A | 8/1980 | Wallshein |
| D256,950 S | 9/1980 | Sable |
| 4,242,085 A | 12/1980 | Wallshein |

(Continued)

FOREIGN PATENT DOCUMENTS

DE 8903611 8/1990

(Continued)

OTHER PUBLICATIONS

U.S. Appl. No. 10/821,699, filed Apr. 9, 2004, Ricketts.

(Continued)

*Primary Examiner*—Cris L Rodriguez
*Assistant Examiner*—Heidi M Eide
(74) *Attorney, Agent, or Firm*—Sheridan Ross P.C.

(57) ABSTRACT

An orthodontic bracket is provided that includes a cover and a base, wherein the cover can be rotated over an arch wire slot in the base portion. The present bracket invention operates to close when a frangible portion is severed upon initiating rotation of the cover, such that the cover rotates about a hinge, which may include a pin or axle. In one embodiment of the invention, the pin or axle can be moved laterally and/or vertically after the frangible portion is severed. Preferably, the bracket is manufactured to form one piece, such as using an injection molding, machining, or casting process. The bracket offers economical advantages because additional subsequent assembly is not required to attach a cover to a base.

14 Claims, 7 Drawing Sheets

U.S. PATENT DOCUMENTS

| | | | |
|---|---|---|---|
| 4,260,375 A | 4/1981 | Wallshein |
| 4,299,569 A | 11/1981 | Frantz |
| 4,302,532 A | 11/1981 | Wallshein |
| 4,354,834 A | 10/1982 | Wilson |
| 4,386,908 A | 6/1983 | Kurz |
| 4,415,330 A | 11/1983 | Daisley et al. |
| 4,419,078 A | 12/1983 | Pletcher |
| 4,430,061 A | 2/1984 | Webb et al. |
| 4,478,577 A | 10/1984 | Warren, Jr. |
| 4,498,867 A | 2/1985 | Kesling |
| 4,527,975 A | 7/1985 | Ghafari et al. |
| 4,529,382 A | 7/1985 | Creekmore |
| 4,531,991 A | 7/1985 | Ziemek et al. |
| 4,545,760 A | 10/1985 | Forster |
| 4,626,209 A | 12/1986 | Tsai et al. |
| 4,659,309 A | 4/1987 | Merkel |
| 4,661,059 A | 4/1987 | Kanno |
| D290,040 S | 5/1987 | Kelly |
| 4,669,981 A | 6/1987 | Kurz |
| D291,919 S | 9/1987 | Reynolds |
| 4,712,999 A | 12/1987 | Rosenberg |
| 4,752,221 A | 6/1988 | Hanson et al. |
| 4,773,853 A | 9/1988 | Kussick |
| 4,781,582 A | 11/1988 | Kesling |
| 4,793,804 A | 12/1988 | Schudy |
| 4,799,882 A | 1/1989 | Kesling |
| 4,819,316 A | 4/1989 | Rossini et al. |
| 4,820,151 A | 4/1989 | Pospisil |
| 4,838,786 A | 6/1989 | Reher et al. |
| 4,854,866 A | 8/1989 | Wilson |
| 4,859,179 A | 8/1989 | Kesling |
| 4,917,602 A | 4/1990 | Broussard |
| 4,927,362 A | 5/1990 | Snead |
| 4,954,080 A | 9/1990 | Kelly et al. |
| 4,963,092 A | 10/1990 | Snead |
| 4,975,052 A | 12/1990 | Spencer et al. |
| 4,997,182 A | 3/1991 | Kussick |
| 5,022,854 A | 6/1991 | Broughton et al. |
| 5,030,089 A | 7/1991 | Kawaguchi |
| 5,044,945 A | 9/1991 | Peterson |
| 5,057,012 A | 10/1991 | Kesling |
| 5,059,119 A | 10/1991 | Snead |
| 5,062,794 A | 11/1991 | Miura |
| 5,066,225 A | 11/1991 | Forbes Jones et al. |
| D322,482 S | 12/1991 | Ianieri et al. |
| 5,095,602 A | 3/1992 | Reher et al. |
| 5,125,831 A | 6/1992 | Pospisil |
| 5,125,832 A | 6/1992 | Kesling |
| 5,127,828 A | 7/1992 | Suyama |
| 5,133,740 A | 7/1992 | Kussick |
| 5,151,028 A | 9/1992 | Snead |
| 5,154,607 A | 10/1992 | Hanson |
| 5,158,452 A | 10/1992 | Franseen et al. |
| 5,160,261 A | 11/1992 | Peterson |
| 5,161,969 A | 11/1992 | Pospisil et al. |
| D331,975 S | 12/1992 | Pospisil |
| 5,203,804 A | 4/1993 | Nikutowski et al. |
| 5,226,814 A | 7/1993 | Allen |
| 5,230,620 A | 7/1993 | Watanabe |
| 5,238,402 A | 8/1993 | Rohlcke et al. |
| 5,242,299 A | 9/1993 | Yoshida |
| D340,523 S | 10/1993 | Barngrover |
| 5,254,002 A | 10/1993 | Reher et al. |
| 5,267,855 A | 12/1993 | Tuneberg |
| 5,269,680 A | 12/1993 | Kawaguchi |
| 5,277,581 A | 1/1994 | Peterson |
| 5,288,229 A | 2/1994 | Huff et al. |
| 5,292,248 A | 3/1994 | Schultz |
| 5,299,934 A | 4/1994 | Suyama |
| 5,302,117 A | 4/1994 | Kraut et al. |
| 5,302,121 A | 4/1994 | Gagin |
| 5,320,525 A | 6/1994 | Forster |
| 5,320,526 A | 6/1994 | Tuneberg |
| 5,322,435 A | 6/1994 | Pletcher |
| 5,362,232 A | 11/1994 | Franseen et al. |
| 5,362,233 A | 11/1994 | Thompson |
| D358,649 S | 5/1995 | Moschik |
| D358,650 S | 5/1995 | Moschik |
| D359,776 S | 6/1995 | Hilgers |
| 5,441,408 A | 8/1995 | Moschik |
| 5,441,409 A | 8/1995 | Tuneberg |
| 5,443,384 A | 8/1995 | Franseen et al. |
| 5,454,716 A | 10/1995 | Banerjee et al. |
| 5,470,228 A | 11/1995 | Franseen et al. |
| 5,522,725 A | 6/1996 | Jordan et al. |
| 5,556,277 A | 9/1996 | Yawata et al. |
| 5,588,833 A | 12/1996 | Risse |
| 5,595,484 A | 1/1997 | Orikasa et al. |
| 5,597,302 A | 1/1997 | Pospisil et al. |
| 5,607,301 A | 3/1997 | Roman |
| 5,616,026 A | 4/1997 | Cash |
| 5,618,175 A | 4/1997 | Reher et al. |
| 5,622,494 A | 4/1997 | Andreiko et al. |
| 5,653,588 A | 8/1997 | Moschik |
| 5,685,711 A | 11/1997 | Hanson |
| 5,692,898 A | 12/1997 | Orikasa et al. |
| 5,707,231 A | 1/1998 | Watt et al. |
| 5,727,941 A | 3/1998 | Kesling |
| 5,729,768 A * | 3/1998 | Fields et al. ............ 396/6 |
| 5,746,592 A | 5/1998 | Nezu et al. |
| 5,746,594 A | 5/1998 | Jordan et al. |
| RE35,863 E | 7/1998 | Sachdeva et al. |
| 5,779,470 A | 7/1998 | Kussick |
| 5,810,583 A | 9/1998 | Doyle |
| 5,829,972 A | 11/1998 | Farzin-Nia |
| 5,857,849 A * | 1/1999 | Kurz ................... 433/10 |
| 5,871,350 A | 2/1999 | Clark et al. |
| 5,885,073 A | 3/1999 | Kussick |
| 5,885,074 A | 3/1999 | Hanson |
| 5,890,891 A | 4/1999 | Doyle |
| 5,908,293 A | 6/1999 | Voudouris |
| 5,915,550 A * | 6/1999 | Gartz ................... 206/308.1 |
| 6,053,729 A | 4/2000 | Brehm et al. |
| 6,086,364 A | 7/2000 | Brunson |
| 6,109,916 A | 8/2000 | Wilcko et al. |
| 6,126,441 A | 10/2000 | Tenti |
| 6,190,165 B1 | 2/2001 | Andreiko et al. |
| 6,193,508 B1 * | 2/2001 | Georgakis ................ 433/11 |
| 6,206,690 B1 | 3/2001 | Vargas |
| 6,217,322 B1 | 4/2001 | Kesling |
| 6,220,857 B1 | 4/2001 | Abels |
| 6,227,849 B1 | 5/2001 | Brehm et al. |
| 6,264,469 B1 | 7/2001 | Moschik |
| 6,280,185 B1 | 8/2001 | Palmer et al. |
| 6,347,939 B2 | 2/2002 | Abels |
| 6,394,798 B1 | 5/2002 | Huff et al. |
| 6,428,314 B1 | 8/2002 | Jones, Jr. et al. |
| 6,461,157 B1 | 10/2002 | Kussick |
| 6,478,579 B1 | 11/2002 | Brusse |
| 6,491,519 B1 | 12/2002 | Clark et al. |
| 6,607,383 B2 | 8/2003 | Abels et al. |
| 6,616,445 B2 | 9/2003 | Abels et al. |
| 6,655,957 B2 | 12/2003 | Abels et al. |
| 6,655,958 B2 | 12/2003 | Abels et al. |
| 6,656,767 B1 | 12/2003 | King et al. |
| 6,659,766 B2 | 12/2003 | Abels et al. |
| 6,659,767 B2 | 12/2003 | Abels et al. |
| 6,695,612 B2 | 2/2004 | Abels et al. |
| 6,705,862 B2 | 3/2004 | Schultz |
| 6,709,268 B2 | 3/2004 | Pospisil et al. |
| 6,776,613 B2 | 8/2004 | Orikasa |
| 6,846,178 B2 | 1/2005 | Freeman, Jr. et al. |
| 6,893,257 B2 | 5/2005 | Kelly |
| 6,910,884 B2 | 6/2005 | Kelly et al. |

| | | |
|---|---|---|
| 6,913,459 B2 | 7/2005 | Fukutomi |
| 7,025,591 B1 | 4/2006 | Kesling |
| 7,033,171 B2 | 4/2006 | Wilkerson |
| 7,210,927 B2 | 5/2007 | Abels et a |
| 7,234,935 B2 | 6/2007 | Abels et al. |
| 2002/0025500 A1 | 2/2002 | Abels et al. |
| 2002/0110771 A1 | 8/2002 | Abels et al. |
| 2002/0110772 A1 | 8/2002 | Abels et al. |
| 2002/0110773 A1 | 8/2002 | Abels et al. |
| 2002/0110774 A1 | 8/2002 | Abels et al. |
| 2002/0110775 A1 | 8/2002 | Abels et al. |
| 2002/0110776 A1 | 8/2002 | Abels et al. |
| 2002/0110777 A1 | 8/2002 | Abels et al. |
| 2002/0110778 A1 | 8/2002 | Abels et al. |
| 2002/0187452 A1 | 12/2002 | Abels et al. |
| 2003/0049582 A1 | 3/2003 | Abels et al. |
| 2005/0003320 A1 | 1/2005 | Freeman et al. |
| 2005/0244777 A1 | 11/2005 | Schultz |
| 2006/0046224 A1 | 3/2006 | Sondhi et al. |

FOREIGN PATENT DOCUMENTS

| | | |
|---|---|---|
| DE | 69228472 | 10/1999 |
| EP | 0317098 | 5/1989 |
| EP | 0379668 | 8/1990 |
| EP | 0389223 | 9/1990 |
| EP | 0397533 | 11/1990 |
| EP | 0875211 | 11/1998 |
| EP | 2130174 | 7/1999 |
| EP | 1332727 | 8/2003 |
| EP | 1359859 | 11/2003 |
| FR | 2497657 | 7/1982 |
| JP | 64-25847 | 1/1989 |
| JP | 1-160547 | 6/1989 |
| JP | 2-147112 | 12/1990 |
| JP | 3-21236 | 1/1991 |
| JP | 2579431 | 2/1997 |
| JP | 11-276504 | 10/1999 |
| WO | WO 91/07925 | 6/1991 |
| WO | WO 92/20296 | 11/1992 |
| WO | WO 2004/039276 | 5/2004 |

OTHER PUBLICATIONS

U.S. Appl. No. 11/123,470, filed May 5, 2005, Wilson.
U.S. Appl. No. 11/695,555, filed Apr. 2, 2007, Wolf.
U.S. Appl. No. 11/740,812, filed Apr. 26, 2007, Muha.
U.S. Appl. No. 11/782,569, filed Jul. 24, 2007, Zakhem.
U.S. Appl. No. 11/852,057, filed Sep. 7, 2007, Smith.
Ricketts "Provocations and Perceptions in Cranio-Facial Orthopedics" RMO, Inc., Denver, CO, USA, 1989, cover and pp. 982-1021.
3M Unitek Corporation Catalog (1990), pp. 1-1, 1-3, 3-7, Figs. A, B.
Ortho Organizers, Inc. Advertisement "Journal of Clinical Orthodontics"; (Sep. 1989), (3 pages).
"Direct Bond Tubes," American Orthodontics, p. 76 (2005).
"Focus on Brackets," Orthodontics Products, pp. 1-2 (Mar. 2005).

* cited by examiner

ORTHODONTIC BRACKET WITH FRANGIBLE COVER MECHANISM

CROSS REFERENCE TO RELATED APPLICATION

The present application claims the benefit of U.S. Provisional Application No. 60/623,715 filed on Oct. 28, 2004, the entire disclosure of which is incorporated herein by reference in its entirety.

FIELD OF THE INVENTION

The present invention is generally related to one-piece orthodontic appliances that have a frangible portion, and more particularly, an orthodontic bracket that includes a frangible mechanism to permit closure of an integral cover.

BACKGROUND OF THE INVENTION

Orthodontic brackets are secured to a patient's teeth for use in selectively straightening the patient's teeth. One type of orthodontic bracket known in the art includes a base having a slot formed thereon. The slot is configured to receive an archwire that extends between different teeth. A separate cover plate is removably attached to the base for use in securing the archwire to the base. One example of the above orthodontic bracket is disclosed in U.S. Pat. No. 4,712,999.

SUMMARY OF THE INVENTION

One object of the present invention is to develop an orthodontic bracket of the kind known in the prior art that is low-cost, simple to manufacture, and compact in construction.

The above and other objects of the present invention are satisfied by the features of the present invention as claimed herein and in particular by an inventive orthodontic bracket having a cover and base that are integrally connected together as a single piece. The inventive orthodontic bracket is relatively low-cost and simple to manufacture. This is due in part to the fact that the orthodontic bracket comprises only one single component which does not have to be assembled. In addition, in one embodiment the inventive orthodontic bracket is made from only one single material, preferably including a metal, plastic or ceramic material. More preferably, the bracket comprises a substantially rigid metal material. Furthermore, the cover is integrally formed with the base so as to prevent unwanted separation. Advantageous embodiments are described in the description, the claims and the figures.

The bracket in accordance with the invention is preferably formed in a self-ligating manner, and the archwire is clamped between the cover and the base. It can be advantageous for this purpose for a plurality of locking recesses to be provided on the cover or the base in order to close the cover at different opening widths. Archwires having different cross-section sizes can be inserted into the slot in this way and be fixed there by closing the cover.

In one embodiment, an orthodontic bracket consists of at least two structural portions comprising a base and a ligation cover. However, the base and ligation cover are not separate, but are integrally formed as one contiguous piece by such methods as casting, injection molding, or machining. Upon being manufactured, the base and ligation over are substantially rigidly connected through one or more webs at a hinge mechanism. The web or webs are frangible, allowing the two structural portions to move relative to each other once the web or webs are sheared, yet after shearing, the base and the ligation cover remain interlocked because of the hinge. The one or more webs can be configured in a variety of geometries. For example, the web or webs may be configured horizontally, vertically, or radially from the pin or axle of the hinge. Alternatively, the web or webs by take on a helical or curved form, extending along at least a portion of the length of the pin or axle of the hinge. At some point along the structure of the web or webs, there may be an area of reduced thickness where the fracturing forces are directed.

In a separate aspect of the invention, the base includes a void space that preferably contains or is operatively associated with the pin or axle of the ligation cover. The shape of the void space and/or the pin or axle may be substantially round or oval, or they may be square, rectangular, triangular, hexagonal, octagonal, trapezoidal, polygonal, a parallelogram, or a free-form combination of lines and arcs. The void space may be substantially the same shape as the pin or axle, or they may be dissimilar in shape.

In a separate aspect of the invention, after forming the bracket, such as by casting, injection molding, or machining, the contiguous one-piece bracket consisting of the base and the ligation cover remains contiguous with an unsheared web or webs until at any time during one of the manufacturing, packaging or application processes that sufficient force is applied to fracture the integrally formed web or webs. After forming the bracket, additional manufacturing processes may include sintering, deburring, polishing, sandblasting, coating or plating, painting, and/or adhesive application. During one of these additional manufacturing processes, the web or webs may be sheared, or the shearing of the web or webs may be performed as part of a different manufacturing processes, or shearing of the web or webs may be performed at a later time.

In a separate aspect of the invention, the bracket preferably includes a latch or interlocking mechanism that is formed as part of the initial one-piece manufacturing process, or as part of a later manufacturing process. The latch or interlocking mechanism allows the ligation cover to be secured to the base at a location spaced apart from the hinge mechanism. In addition, the latch or interlocking mechanism allows an archwire placed within the bracket to be ligated when the ligation cover is closed.

Various embodiments of the present invention are set forth in the attached figures and in the detailed description of the invention as provided herein and as embodied by the claims. It should be understood, however, that this Summary of the Invention may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

The present invention is described below by means of example embodiments and with reference to the enclosed drawings, in which are shown.

While the following disclosure describes the invention in connection with those embodiments presented, one should understand that the invention is not strictly limited to these embodiments. Furthermore, one should understand that the drawings are not necessarily to scale, and that in certain instances, the disclosure may not include details which may be necessary to manufacture particular embodiments, such as conventional details of fabrication and assembly.

DETAILED DESCRIPTION OF THE INVENTION

Figure 1:
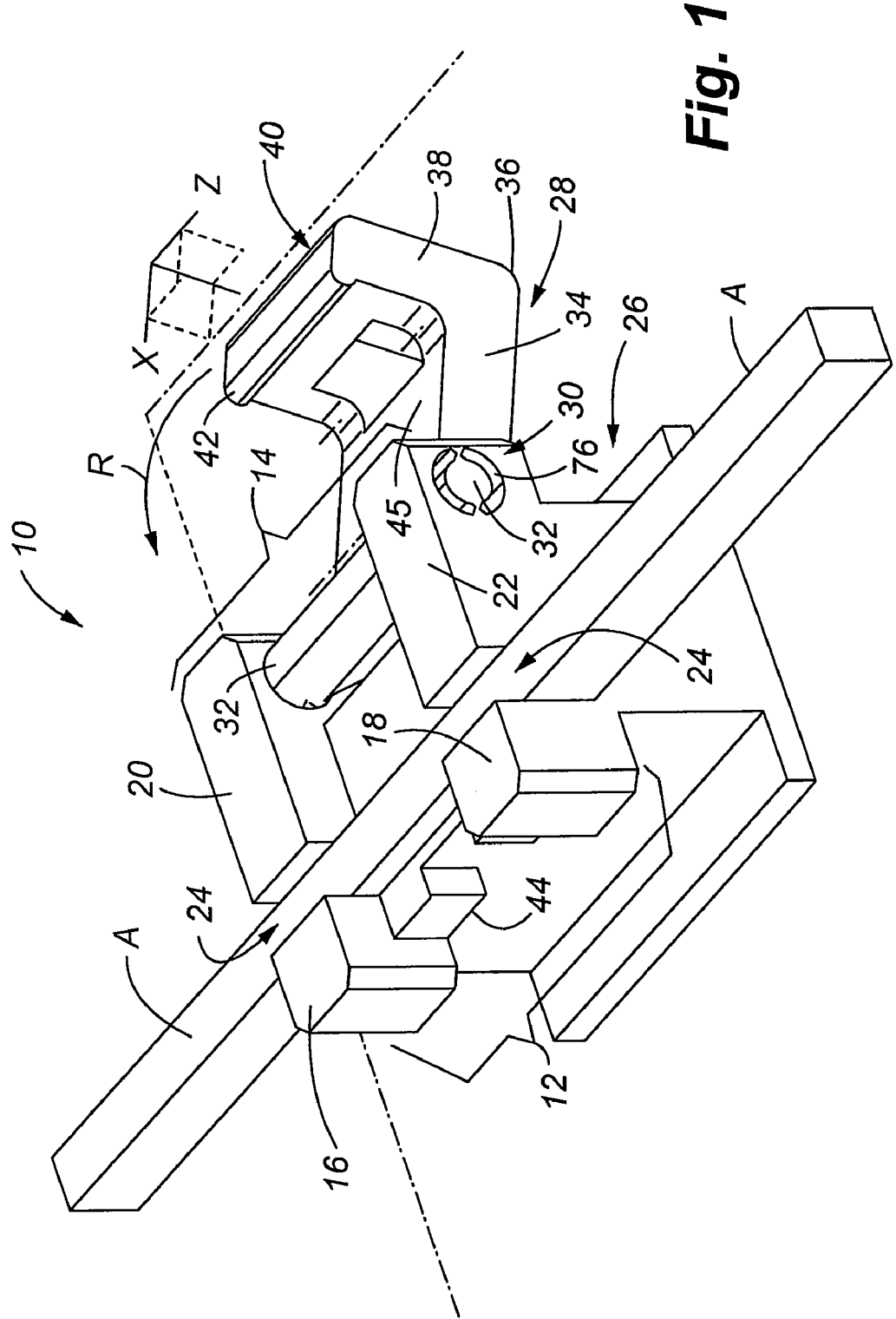
FIG. 1 is a front and side perspective view of an orthodontic bracket that includes an embodiment of the present invention.
Figure 2:
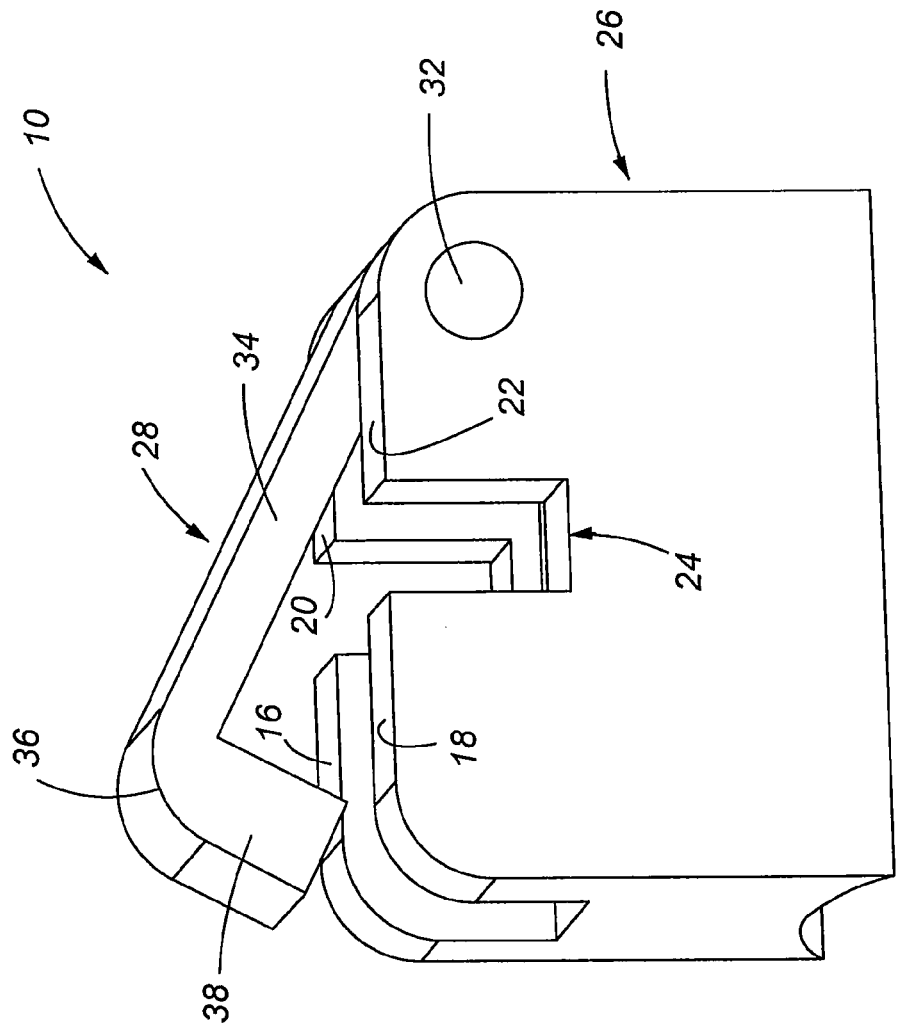
FIG. 2 is a side perspective view of an embodiment of the present invention.
Figure 3:
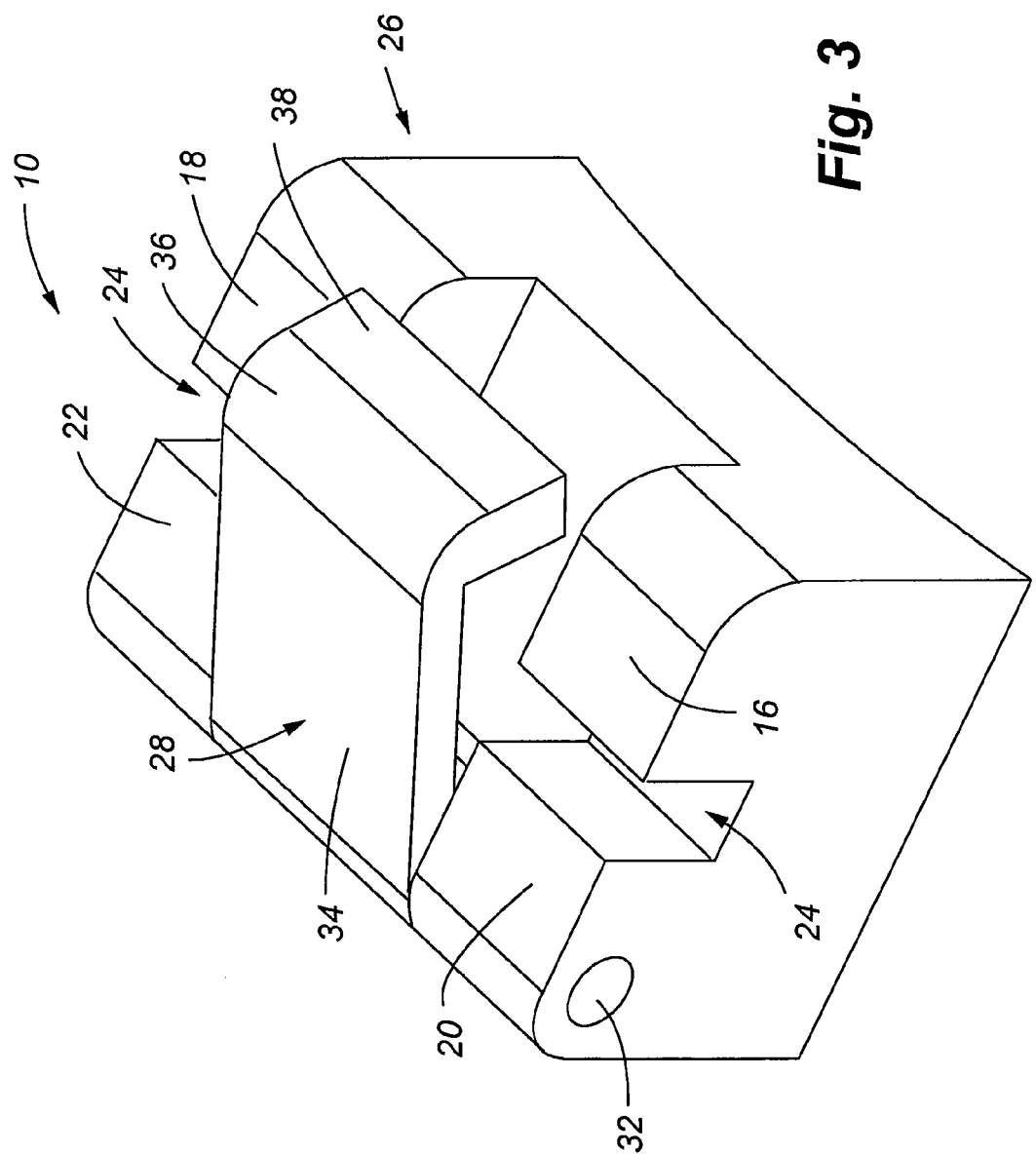
FIG. 3 is a top and side perspective view of an embodiment of the present invention.

Referring now to FIG. 1, a perspective view of the side and front of an orthodontic twin bracket 10 is shown. The bracket 10 includes a gingival tie wing 12 and an occlusal tie wing 14. The gingival tie wing 12 includes a mesial wing tip 16 and a distal wing tip 18. Similarly, the occlusal tie wing 14 includes a mesial wing tip 20 and a distal wing tip 22. Located between the gingival tie wing 12 and the occlusal tie wing 14 is a mesiodistal-extending archwire slot 24 holding archwire A. FIG. 1 also illustrates the two basic structures of the bracket 10, that is, body 26 and cover 28. The cover 28 may comprise a ligation cover; that is, a cover that ligates the archwire A.

For the one-piece bracket embodiment, body 26 is preferably integrally formed together with cover 28 during manufacture of the bracket 10. More particularly, in a preferred embodiment, body 26 and cover 28 are integrally molded such as by injection molding, casting, or machining or otherwise manufactured as a single unit, such that the body 26 and cover 28 are an integral piece.

Still referring to FIG. 1, the cover 28 of the bracket 10 is operatively associated with the body 26. More particularly, a hinge mechanism 30 preferably interconnects the cover 28 to the body 26, wherein the hinge mechanism 30 allows the cover 28 to be rotated in the direction of rotational arrow R toward the body 26. The hinge mechanism 30 preferably includes a rotatable member, axle or pin 32 that interconnects the cover 28 to the mesial and distal wings of the body 26. For the example shown in FIG. 1, the pin 32 interconnects the cover 28 to the mesial wing tip 20 and the distal wing tip 22 of the occlusal tie wing 14. For the perspective view of the bracket 10 shown in FIG. 1, the pin 32 can be seen within the distal wing tip 22 of the occlusal tie wing 14.

Still referring to FIG. 1, the cover 28 preferably includes a front portion 34, a bend 36 and a lateral portion 38. An end portion 40 of the lateral portion 38 preferably includes a cover latch member 42 that cooperates with a base latch member 44 upon rotating the cover 28 and engaging the cover latch member 42 with base latch member 44. The cover 28 preferably ligates the archwire A upon rotating the cover 28 and engaging the cover latch member 42 with the base latch member 44.

The cover interior surface 45 of the front portion 34 may include at least one projection (not shown) to provide limited surface contact between the cover 28 and archwire A. In addition, the base 26 may also include at least one projection (not shown) to provide limited surface contact between the base 26 and archwire A.

Figure 4:
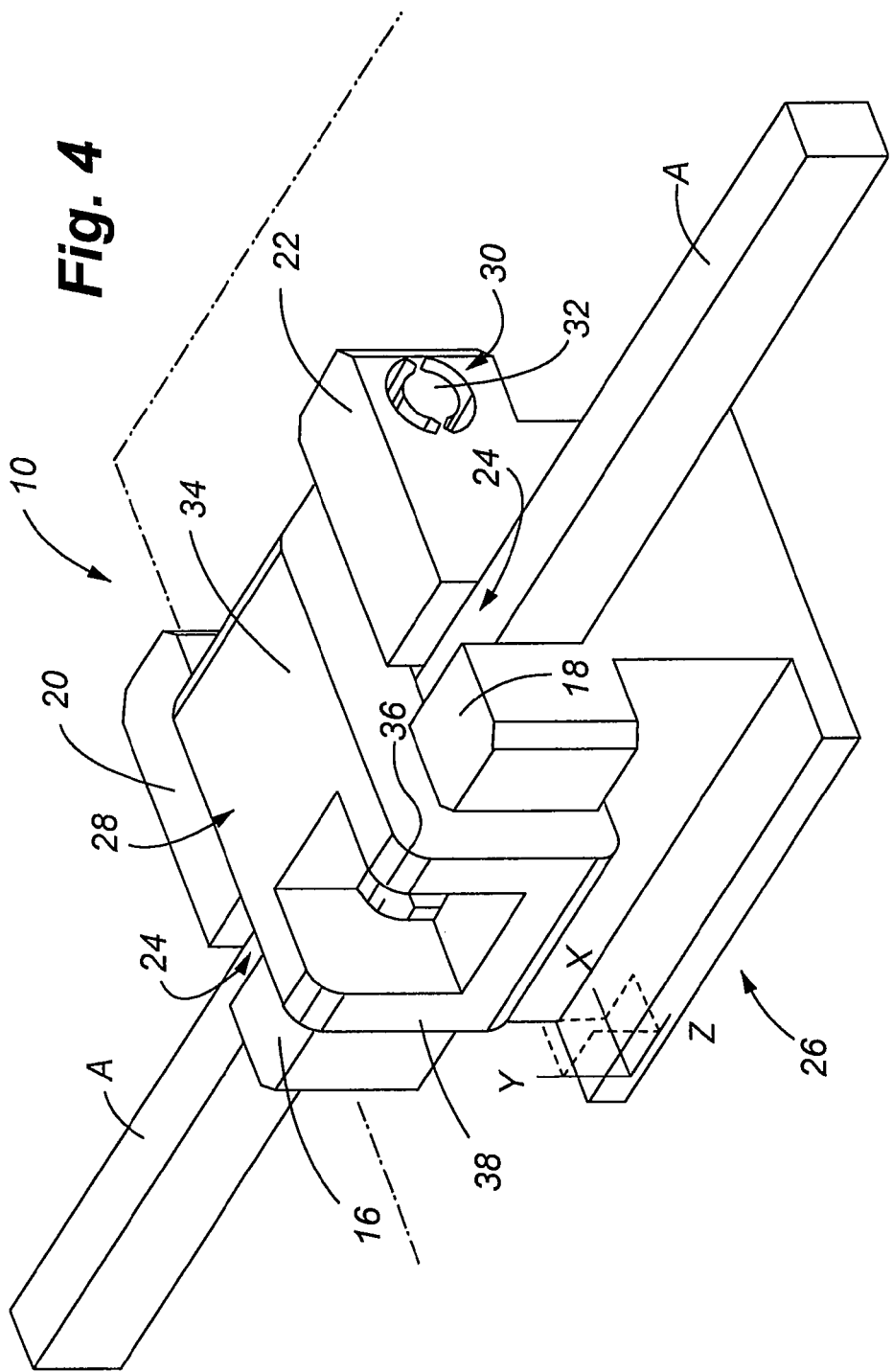
FIG. 4 is a front and side perspective view of the device shown in FIG. 1 with an archwire in an archwire slot and the cover closed over the archwire.

Referring now to FIG. 4, bracket 10 is shown in the closed position. Archwire A within archwire slot 24 (also referred to as "locking recesses") is ligated between the base 26 and the cover 28.

Referring now to FIG. 4, bracket 10 is shown in the closed position. Archwire A within archwire slot 24 is ligated between the base 26 and the cover 28.

Figure 5A:
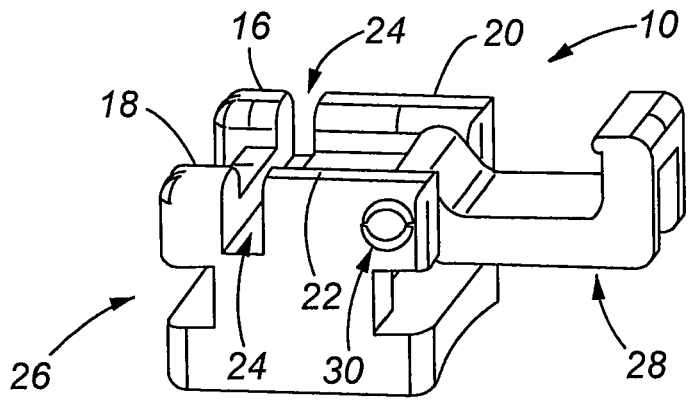
FIGS. 5a-5c are a series of side perspective views of an embodiment of the present invention with its cover in a fully open, partially closed, and closed position.
Figure 5B:
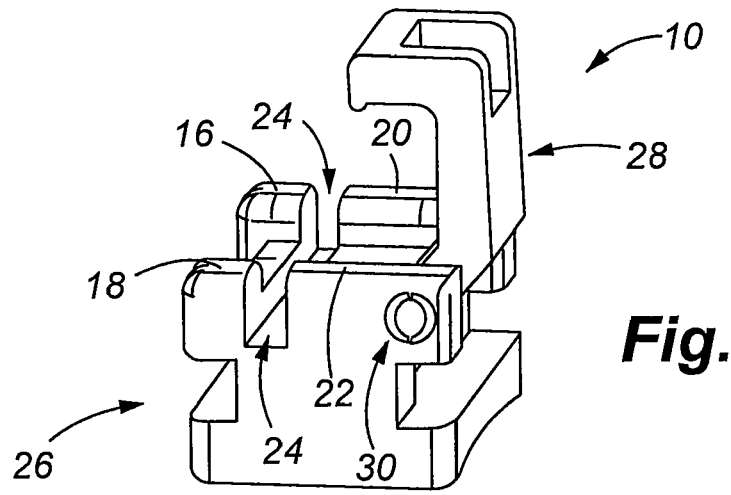
Figure 5C:
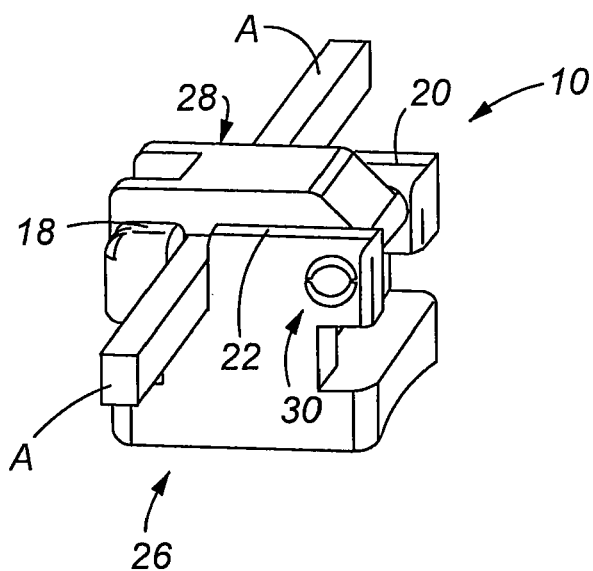

In one embodiment of the present invention, the hinge mechanism 30 preferably includes a frangible portion. More particularly, the hinge mechanism 30 includes a part that is frangible or breaks upon rotating the cover 28 to latch with the base 26. Since the entire bracket 10 is preferably manufactured as single integral unit, the frangible portion is also produced as part of process of making the bracket 10. Referring now to FIGS. 5a-5c, a series of side perspective views of a bracket 10 with a frangible hinge mechanism 30 are shown. FIG. 5a depicts the bracket 10 having a cover 28 in a fully open position. FIG. 5b depicts the bracket 10 with the frangible hinge mechanism 30 having been sheared, and the cover 28 in a partially closed position. FIG. 5c depicts the cover 28 in a fully closed position over an archwire A in the archwire slot 24.

Figure 6A:
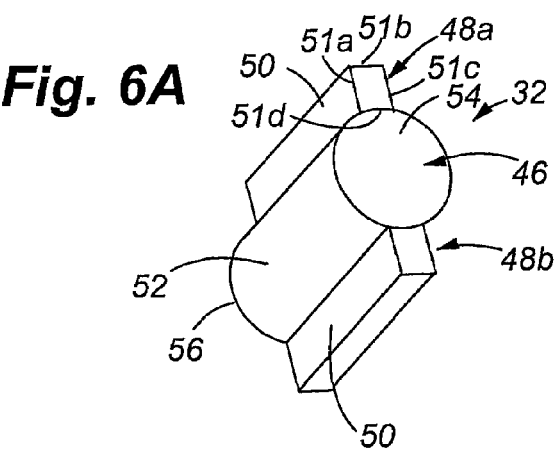
FIGS. 6a-6d are perspective views of possible alternate configurations of the axle and frangible portions interconnected thereto.

Referring now to FIG. 6a, a first embodiment of a pin 32 having a frangible portion is shown. More particularly, FIG. 6a illustrates a pin 32 that is substantially a cylinder 46, with two frangible portions. The first frangible portion 48a is fin or web 50 that extends outward from the exterior lateral surface 52 of the cylinder 46. The web 50 extends the entire length of the cylinder 46, or from a first pin end 54 to a second pin end 56; however, the web 50 may occupy only a limited portion of the length of cylinder 46. The web 50 is preferably continuous or solid. However, it may include perforations or open segments between the first pin end 54 and second pin end 56. The web 50 is sized so that at least a portion of it can break when the cover 28 is rotated toward the base 26.

Although not required, the pin 32 of FIG. 6a may include more than one frangible portion. More particularly, the pin 32 may include a plurality of frangible portions, such as a second frangible portion 48b that also extends the entire length of the cylinder 46. For the device shown in FIG. 6a, the second frangible portion 48b is also a fin or web 50, and is located at a position along the exterior lateral surface 52 of the cylinder 46 that is substantially at a diametrically opposite location as the first frangible portion 48a. However, the second frangible portion 48b could alternatively be located at a different position along the exterior lateral surface 52 of the cylinder 46. For example, the second frangible portion 48b may be positioned at 45 degrees, 60 degrees, 90 degrees, or 120 degrees from the first frangible portion 48a. Furthermore, as shown in FIG. 6a, the web 50 of the second frangible portion 48b may be substantially the same shape as the web 50 of the first frangible portion 48a, or it may be a different shape.

Figure 7A:
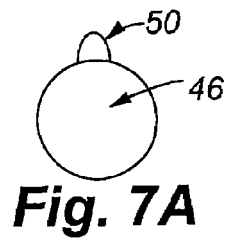
FIGS. 7a-7d are side elevation views of still other alternate configurations of the axle and frangible portions interconnected thereto.
Figure 7B:
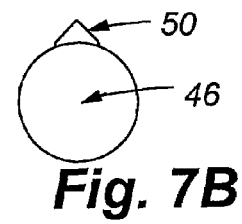
Figure 7C:
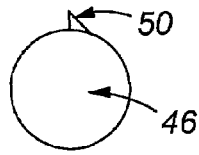
Figure 7D:
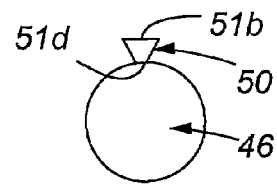

The web 50 shown in FIG. 6a includes a web first side 51a, a web second side 51b a web third side 51c, and a web base 51d that abuts the cylinder 46. The web first side 51a is orientated substantially perpendicular or at about a 90 degree angle to the web second side 51b, and the web second side 51b is orientated substantially perpendicular or at about a 90 degree angle to the web third side 51c. In addition, the web first side 51a is substantially parallel to the web third side 51c, and the web second side 51b is located opposite the web base 51d. However, the web 50 may take on an alternate shape, such as a curved form with no sharp corners, such that shown in FIG. 7a. Alternatively, the web 50 may take on a pointed shape, such as that shown in FIGS. 7b and 7c. In addition, as shown in FIG. 7d, the web 50 may have a thinner web base 51d adjacent the exterior surface 52 of the cylinder 46 as compared to a width of a surface at a further radial distance, such as width of second side 51b. Such web shapes offer advantages for providing lesser or greater resistance against shearing. Thus, a web 50 can be customized to provide a desired amount of strength, and the web 50 may be a variety of possible shapes, including geometric shapes, curved shapes and random shapes.

Figure 6B:
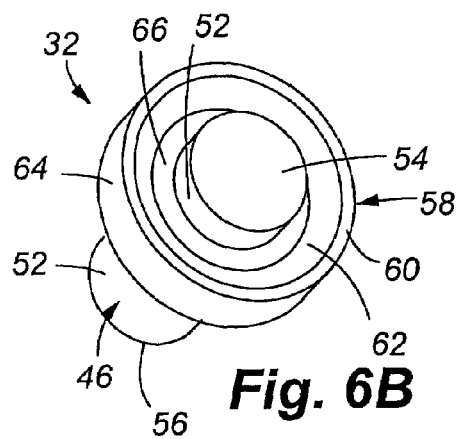

Referring now to FIG. 6b, an alternate embodiment of a pin 32 is shown, wherein the pin 32 includes a frangible portion 58. The frangible portion 58 of FIG. 6b is a radial web 60 that substantially circumscribes the cylinder 46. In addition, the frangible portion 58 is preferably closer to first pin end 54 than second pin end 56. The frangible portion 58 may include a partially wedge shaped portion 62. In addition, the frangible portion 58 may include a radial exterior surface 64 that is longer in longitudinal length that an interior portion 66.

Figure 6D:
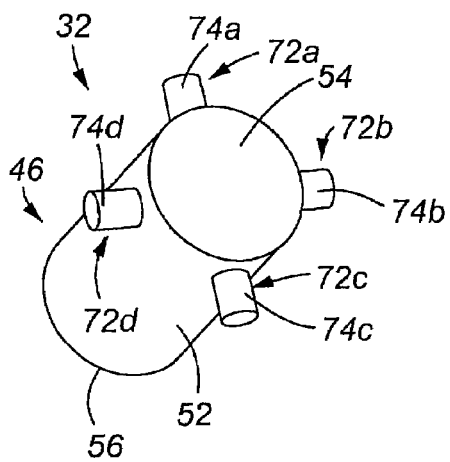
Figure 6C:
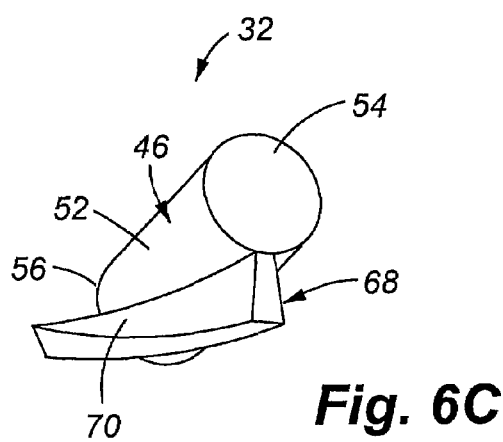

Referring now to FIG. 6c, an alternate embodiment of a pin 32 is shown, wherein the pin 32 includes a frangible portion 68. The frangible portion 68 is a spiral web or curvilinear member 70 that extends along the exterior lateral surface 52 of the cylinder 46. The curvilinear member 70 may be continuous, or it may be perforated and segmented along its length. In addition, the curvilinear member 70 may be of uniform curvature and shape, or it may be variable in curvature and shape. As shown in FIG. 6c, the frangible portion 68 extends from the first pin end 54 to the second pin end 56; however, the frangible portion 68 may extend along only a portion of the length of the cylinder 46.

Referring now to FIG. 6d, an alternate embodiment of a pin 32 is shown, wherein the pin 32 includes at least one frangible portion, and more preferably, a plurality of frangible portions 72a-72d. As shown in FIG. 6d, the frangible portions 72a-72d comprise pegs 74a-74d that project from the exterior lateral surface 52 of cylinder 46. The pegs 74a-74d are substantially cylindrical shaped members; however, they can be a variety of shapes, including rectangular blocks. In addition, the individual frangible portions 72a-72d may be different shapes, for example, frangible portion 72b can be a web 30, such as that shown in FIG. 6a, and frangible portion 72c can be a curvilinear member 70, such as that shown in FIG. 6c. Similar to the frangible portions 48a, 48b, 58, and 68 shown in FIGS. 6a-6c, the frangible portions 72a-72d of pin 32 of FIG. 6d are sized to shear but remain connected to the bracket 10, including during rotation of the cover 28 toward the base 26, thereby allowing the cover 28 to fully rotate and engage and latch with base 26, but still remain an integral piece.

Referring still to FIGS. 6a-6d, it is further noted that the pin 32 can have a circular shape in cross section, such that frangible portions are operatively associated with a cylinder 46, as described above and shown in FIGS. 6a-6d. However, the central portion of the pin 32 can also take on a variety of shapes, such as a cone shaped axle, or a faceted or multi-sided axle that includes a number of planar surfaces that form its exterior lateral surface.

Figure 8A:
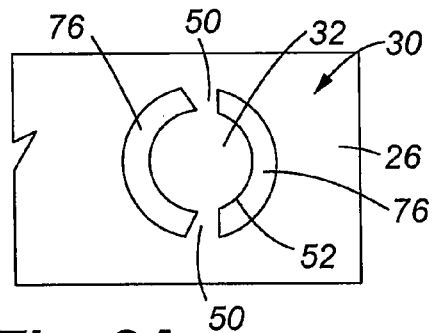
FIGS. 8a-8e are side elevation views of possible configurations for the pin or axle and the void space structure associated with the present invention.

Referring now to FIG. 8a, a detailed side elevation view of the hinge mechanism 30 of FIGS. 1-5 is shown. The circular cross section of the pin 32 is shown, with the webs 50 that are operatively associated with the pin 32. With the exception of the webs 50, void space 76 surrounds the circumferential perimeter of the pin 32. When the cover 28 is first rotated toward the base 26, the webs are sheared and the pin 32 rotates. Continuing to rotate the cover 28 toward the base 26 allows the cover latch member 42 to engage the base latch member 44, as shown in FIG. 4.

In a separate aspect of the invention, a pin is provided that can be moved vertically and/or laterally, and which preferably also rotates. More specifically, a pin 32 is provided that can be moved vertically and/or laterally within the base 26. Several different embodiments of the present invention are discussed below that illustrate this aspect of the invention. In general, the pin 32, can be located in a variety of orientations, and it is to be understood that the pin position in the figures is only exemplary.

Figure 8B:
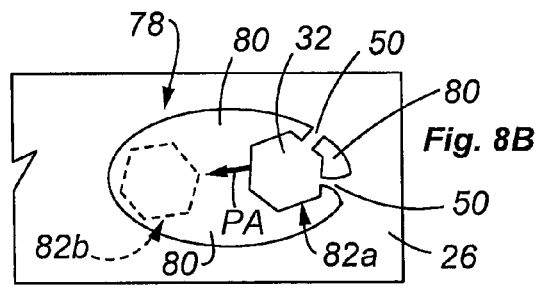

Referring now to FIG. 8b, a detailed side elevation view of an alternate embodiment of a hinge mechanism is shown. Hinge mechanism 78 includes a substantially oblong, and more particularly, a substantially elliptical-shaped void space 80 with a pin 32 located in a first position 82a, as represented by solid lines. The pin 32 is moveable within the void space 80. For example, the pin 32 can be shifted to a second position 82b, as represented in dashed lines. Pin 32 may be a variety of cross sectional shapes, such as circular, rectangular, square, elliptical, triangular, polygonal, etc. For the example depicted in FIG. 8b, the pin 32 is a hexagon in cross section.

The hinge mechanism 78 includes two webs 50. However, instead of two webs 50 as depicted, the hinge mechanism 78 could alternatively be constructed of only one web, or it may be constructed of more than two webs. The hinge mechanism 78 is capable of moving inside the void space 80 because the void space 80 is larger than the pin 32. In use, the cover that is interconnected to the pin 32 is rotated, thereby shearing the connection of the webs 50 with the pin 32. The pin 32 can then be rotated. In addition, the pin can be shifted within the void space 80. For example, the pin 32 can be shifted in accordance with position arrow PA from a first position 82a to second position 82b, where the pin 32 in the second position 82b is laterally and/or vertically displaced relative to the first position 82a. The ability of the pin 32 to move laterally and/or vertically allows for the cover 28 to be shifted during the process of latching the cover 28 to the base 26. For example, if a substantially rigid and/or substantially inelastic material is used to form the base 26 and/or the cover 28, the cover latch member 42 that cooperates with a base latch member 44 may not be able to deflect sufficiently to allow the cover 28 latch to the base 26. If required, a laterally and/or vertically moveable pin 32 allows the cover 28 some motion to permit the latching process. Furthermore, even if sufficiently deformable materials are used to construct the base 26 and/or the cover 28, the moveable pin 32 may provide reduced friction interaction between the bracket 10 and the archwire A.

Figure 8C:
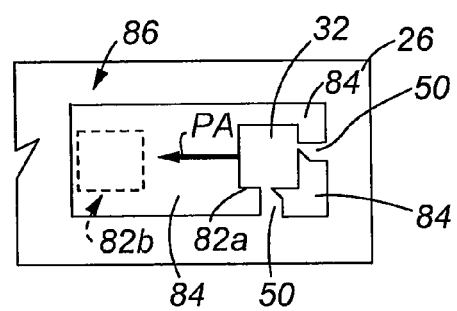

Referring now to FIG. 8c, a substantially square shaped pin 32 is situated within a substantially rectangular-shaped void space 84 of hinge mechanism 86. The pin 32 is located in a first position 82a, as represented by solid lines, when attached to webs 50, and the pin 32 is also shown in a second position 82b, as represented in dashed lines. The pin 32 may rotate and may move laterally after the webs are sheared that initially hold the pin 32 in place.

Figure 8D:
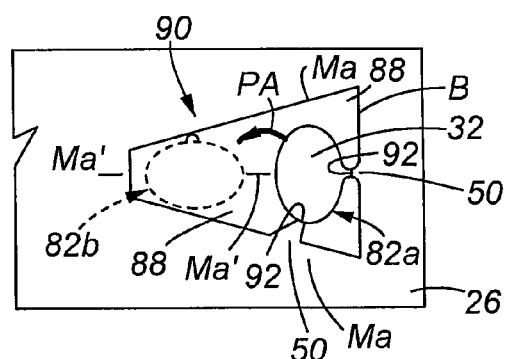

In a separate aspect of the invention, the pin shape and the void space shape may be preferentially structured to place the pin in a restricted second position. That is, the pin shape and void space may compliment each other, whereby the pin is placed in an area of the void space that limits the lateral and/or vertical movement of the pin when the webs are sheared and the pin is in its second position. Referring now to FIG. 8d, a substantially elliptical-shaped pin 32 is situated within a substantially trapezoidal-shaped void space 88 of hinge mechanism 90. The pin 32 may rotate and may move laterally after the webs are sheared that initially hold the pin 32 in place. More particularly, the pin 32 is located in a first position 82a, as represented by solid lines, when attached to webs 50. The first position 82a places the pin 32 generally in the wide portion of the trapezoid-shaped void space 88, where the major axis Ma-Ma of the elliptical shaped pin 32 is oriented substantially parallel to the base B of the trapezoid-shaped void space 88. Again, it is noted that the pin 32 could be located in a variety of orientations, and it is to be understood that the first position 82a of pin 32 in the figure is only exemplary. The pin 32 is also shown located in a second position 82b, as represented in dashed lines. In the second position, the pin 32 is shown with it major axis Ma'-Ma' substantially perpendicular to the base B. Furthermore, the pin 32 is confined by the unparallel edges of the trapezoid-shaped void space 88. Thus, the pin has restricted motion in a vertical direction, where vertical is defined in FIG. 8d as substantially parallel to base B of the trapezoid-shaped void space 88. In a sense, the narrowing shape of the trapezoid-shaped void space 88 acts as a funnel, whereby the pin 32 is sheared from webs 50, such as along shear planes 92, and the pin 32 is then rotated by rotating the cover 28, and the pin 32 is moved laterally to a more confined position within the void space 88, such as second position 82b. The shape of the void space thereby limits movement of the pin in the second position, and thus restricts movement of the pin and thus the cover during rotation, thereby helping to ensure a proper alignment of the cover 28 when latching to the base 26.

Figure 8E:
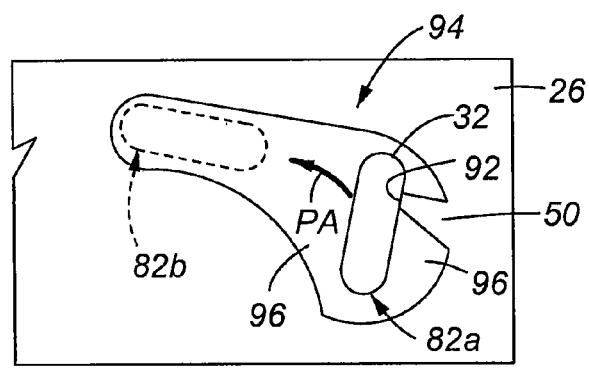

Referring now to FIG. 8e, yet a further embodiment of the hinge mechanism is illustrated. Hinge mechanism 94 includes an oblong-shaped pin 32 situated within an unsymmetrical-shaped void space 96. The pin 32 may rotate and may move laterally after the single web 50 is sheared which initially holds the pin 32 in place. More particularly, the pin 32 is located in a first position 82a, as represented by solid lines, when attached to web 50. The first position 82a places the pin 32 generally in a wide portion of the unsymmetrical-shaped void space 96. Again, it is noted that the pin 32 could be located in a variety of orientations, and it is to be understood that the first position 82a of pin 32 in the figure is only exemplary. The pin 32 is also shown located in a second position 82b, as represented in dashed lines. In the second position 82b, the pin 32 is confined within a restricted area of the void space 96. Again, the narrowing shape of the unsymmetrical-shaped void space 96 acts as a funnel, whereby the pin 32 is sheared from web 50, such as along shear plane 92, and the pin 32 is then rotated by rotating the cover 28, and the pin 32 is moved laterally to a more confined position within the void space 96, such as second position 82b. The shape of the void space thereby limits movement of the pin in the second position, and thus restricts movement of the pin and thus the cover during rotation, thereby helping to ensure a proper alignment of the cover 28 when latching to the base 26. Accordingly, FIGS. 8b-8e show that the void space can take on a variety of different shapes, wherein the void space shape directs the movement of the pin 32 during rotation of the cover 28.

After casting, injection molding, or machining the contiguous one-piece bracket 10 that includes the body 26 and the cover 28, the bracket 10 remains a contiguous one-piece bracket to allow for other manufacturing processes, such as sintering, deburring, polishing, sandblasting, coating or plating, and/or paint or adhesive application.

To provide further written description and enablement support for the present invention, especially as to how appliances are manufactured, etc., the following U.S. patents are incorporated herein by reference in their entireties: U.S. Pat. Nos. 6,695,612; 6,659,767; 6,659,766; 6,655,958; 6,655,957; 6,616,445; 6,607,383; 6,347,939; 6,220,857; 4,712,999; and 4,419,078.

To assist in the understanding of the present invention the following list of components and associated numbering found in the drawings is provided herein:

| Number | Component |
|---|---|
| 10 | bracket |
| 12 | gingival tie wing |
| 14 | occlusal tie wing |
| 16 | mesial wing tip (of the gingival tie wing) |
| 18 | distal wing tip (of the gingival tie wing) |
| 20 | mesial wing tip (of the occlusal tie wing) |
| 22 | distal wing tip (of the occlusal tie wing) |
| 24 | archwire slot |
| 26 | body |
| 28 | cover/ligation cover |
| 30 | hinge mechanism |
| 32 | pin or axle |
| 34 | front portion |
| 36 | bend |
| 38 | lateral portion |
| 40 | end portion |
| 42 | cover latch portion |
| 44 | base latch portion |
| 45 | cover interior surface |
| 46 | cylinder |
| 48a | first frangible portion |
| 48b | second frangible portion |
| 50 | web |
| 51a | web first side |
| 51b | web second side |
| 51c | web third side |
| 51d | web base |
| 52 | exterior lateral surface (of cylinder) |
| 54 | first pin end |
| 56 | second pin end |
| 58 | frangible portion |
| 60 | radial web |
| 62 | partially wedge shaped portion |
| 64 | radial exterior surface |
| 66 | interior portion |
| 68 | frangible portion |
| 70 | curvilinear member |
| 72a-72d | frangible portions |
| 74a-74d | pegs |
| 76 | void space |
| 78 | hinge mechanism |
| 80 | elliptical-shaped void space |
| 82a | pin first position |
| 82b | pin second position |
| 84 | rectangular-shaped void space |
| 86 | hinge mechanism |
| 88 | trapezoidal-shaped void space |
| 90 | hinge mechanism |
| 92 | shear plane |
| 94 | hinge mechanism |
| 96 | unsymmetrical-shaped void space |
| A | archwire |
| B | base (of trapezoidal-shaped void space) |
| Ma-Ma | major axis of elliptical-shaped pin |
| PA | position arrow |
| R | rotational arrow |

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An orthodontic bracket comprising:
    at least two structural portions comprising a base and a ligation cover integrally formed as one contiguous piece to prevent unwanted separation, said base and ligation cover substantially rigidly connected through one or more webs at a hinge mechanism having one of a pin or axle, said bracket adapted to receive an archwire between the cover and the base, said one or more webs being frangible to allow the at least two structural portions to move relative to each other when said one or more webs are sheared, said base and ligation cover remaining interlocked by said hinge mechanism after said one or more webs are sheared;
    a plurality of locking recesses provided on one of the cover or the base that allow archwires having different cross-section sizes to be inserted and fixed in one of said plurality of locking recesses by closing the cover to different opening widths;
    an interlocking mechanism operatively associated with the ligation cover to secure said ligation cover to the base at a location spaced apart from the hinge mechanism when the ligation cover is closed;
    wherein said one or more webs are configured in one of a horizontal, vertical, or radial position from said pin or axle and have one of a helical or curved form extending along at least a portion of said hinge, said one or more webs having an area of reduced thickness where fracturing forces are directed; and
    wherein said base has at least one void space operatively associated with one of said pin, axle or ligation cover, said void space having a shape selected from the group consisting of round, oval, square, rectangular, hexagonal, trapezoidal, and polygonal.

2. The bracket as claimed in claim 1, wherein said one or more webs are interconnected to said pin prior to shearing said one or more webs.

3. The bracket as claimed in claim 2, wherein said one or more webs comprise a breakable material proximate the void space and said pin.

4. The bracket as claimed in claim 1, wherein said bracket comprises a metal.

5. The bracket as claimed in claim 1, wherein said void space is substantially elliptical in shape.

6. The bracket as claimed in claim 1, wherein said void space is substantially rectangular in shape.

7. The bracket as claimed in claim 1, wherein said void space is substantially trapezoidal in shape.

8. The bracket as claimed in claim 1, wherein said void space is substantially unsymmetrical in shape.

9. The bracket as claimed in claim 1, wherein said void space includes a narrowing shape.

10. The bracket as claimed in claim 1, wherein said pin is laterally moveable after said pin is sheared from said one or more webs.

11. The bracket as claimed in claim 1, wherein said pin is moveable from a first position to a second position after said pin is sheared from said one or more webs.

12. The bracket as claimed in claim 11, wherein said second position is a lateral movement relative to said first position.

13. The bracket as claimed in claim 11, wherein said second position is a vertical movement relative to said first position.

14. The bracket as claimed in claim 12, wherein said second position further comprises a vertical movement relative to said first position.

* * * * *